United States Patent
Triel

(10) Patent No.: US 9,427,548 B2
(45) Date of Patent: *Aug. 30, 2016

(54) METHOD FOR ROUNDING EDGES OF OPENINGS IN A TUBULAR BODY AND A PRODUCT THEREOF

(71) Applicant: Coloplast A/S, Humlebaek (DK)

(72) Inventor: Egon Triel, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 378 days.

This patent is subject to a terminal disclaimer.

(21) Appl. No.: 13/907,978

(22) Filed: Jun. 3, 2013

(65) Prior Publication Data

US 2013/0264745 A1    Oct. 10, 2013

Related U.S. Application Data

(63) Continuation of application No. 12/528,626, filed on Aug. 26, 2009, now Pat. No. 8,475,699.

(51) Int. Cl.
*B29C 59/02* (2006.01)
*A61M 25/00* (2006.01)
(Continued)

(52) U.S. Cl.
CPC ....... *A61M 25/0015* (2013.01); *A61M 25/007* (2013.01); *B29C 67/0048* (2013.01); *B26F 1/0015* (2013.01); *B29C 43/361* (2013.01); *B29C 2043/3615* (2013.01); *B29K 2105/258* (2013.01);

(58) Field of Classification Search
CPC ............ B29C 67/004; B29C 67/0044; B29C 67/0048; A61M 25/0015
USPC ....... 264/319, 320, 293, 635, 154, 155, 156, 264/332
See application file for complete search history.

(56) References Cited

U.S. PATENT DOCUMENTS 2,972,779 A * 2/1961 Cowley ............ A61M 25/0015
                                                        216/53
4,407,304 A    10/1983 Lieber et al.
(Continued)

FOREIGN PATENT DOCUMENTS

DE   102004008709 A1   9/2005
EP        384476 A1    8/1990
(Continued)

OTHER PUBLICATIONS

Notice of Opposition mailed on Feb. 24, 2016, against European Patent Application No. 08717241.7.

*Primary Examiner* — Stella Yi
(74) *Attorney, Agent, or Firm* — Coloplast Corp., Coloplast A/S; Nick Baumann

(57) ABSTRACT

A method of treating a hole formed in a catheter includes providing the catheter with an opening formed in a wall of the catheter from an external surface of the catheter to an internal surface of a lumen of the catheter such that the catheter has a sharp external edge formed between the external surface and the opening and a sharp internal edge formed between the opening and the internal surface of the lumen of the catheter. The method additionally includes pushing a proximal end of a mandrel into the opening formed in the wall of the catheter and rounding the sharp external edge of the opening formed in the wall of the catheter with a distal end of the mandrel. The method further includes maintaining the sharp internal edge formed between the opening and the internal surface of the catheter.

11 Claims, 3 Drawing Sheets

Figure 1:
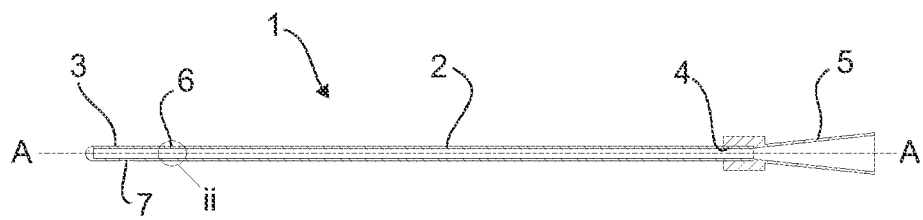

(51) Int. Cl.
*B29C 67/00* (2006.01)
*B26F 1/00* (2006.01)
*B29C 43/36* (2006.01)
*B29K 105/00* (2006.01)
*B29L 31/00* (2006.01)

(56) References Cited

U.S. PATENT DOCUMENTS

2004/0006318 A1 1/2004 Periakaruppan et al.

2004/0193143 A1 9/2004 Sauer
2005/0192560 A1 9/2005 Walls et al.

FOREIGN PATENT DOCUMENTS

| | | |
|---|---|---|
| FR | 0790544 | 11/1935 |
| GB | 2230702 A1 | 10/1990 |
| WO | 2008155145 A1 | 12/2008 |

* cited by examiner

METHOD FOR ROUNDING EDGES OF OPENINGS IN A TUBULAR BODY AND A PRODUCT THEREOF

FIELD OF THE INVENTION

The present invention relates to a method for rounding and/or smoothing openings in a tubular body, especially openings such as eyes or eyelets, in a catheter and a product thereof

BACKGROUND

Persons having problems emptying their bladders often use catheters to aid urination. Furthermore, it is common today to use an intermittent catheter, which the user can operate by him/herself without the need for assistance from a second person and only when voiding of the bladder is needed. Thus, the need of permanent catheterisation is avoided and more freedom and quality of life is obtained for the user.

A typical intermittent catheter comprises a tubular body having a proximal end, which is initially inserted into the urethra and a distal end opposite the proximal end. At least one opening at the proximal end is in fluid connection with an opening at the distal end. The opening at the distal end is usually coaxially connected to a so-called connector. A connector is generally a conical shaped tubular body tapering outwardly from the distal end of the catheter. The connector may be used to connect the catheter to an extension tube or a urine bag and a user can use the connector to operate the catheter. By holding the connector only the user may guide the catheter into the urethra, thereby avoiding touching the catheter body and thus reducing the risk of contaminating the tubular body.

In use, the user will typically grab hold of the connector and guide the catheter body into the urethra, starting by inserting the proximal end. When the opening at the proximal end enters the bladder, urine will flow into the proximal end through the tubular body and out through the connector.

To reduce the risk of injuring the mucosa, the wall of the urinary channel, it is common to dose off and round the proximal end of the tubular body, giving it a smooth tip which is gentle on the mucosa. Inlet openings, i.e. the openings at the proximal end, are instead provided on the side of the tubular body as so-called catheter eyes or eyelets. Such eyelets can be provided in different ways for example they can be cut, drilled, stamped out or molded together with the catheter when the catheter is produced by molding. Although the location of such eyelets reduces the risk of tearing the mucosa considerably, there is still need for improvement as the mucosa is very vulnerable and the edge of the eyelet and irregularities surrounding the eyelet might cause injury to the mucosa.

U.S. Pat. No. 3,149,186 discloses a method from making an improved catheter for peritoneal dialysis. The distal end of the catheter is provided with seventy to one hundred fifty small holes, having diameters ranging between 0.010 to 0.025 inches. The holes are punched by heated pins, where the temperature of the pins is adjusted to a point where they soften, but do not melt, the wall of the thermoplastic tubing. In this way, the plastic material displaced by the pin is pushed inwardly forming an indented outer surface and an inner collar or flange.

GB patent 1 580 924 discloses a method especially applicable to the forming of lateral holes in plastics tubing of small diameter. The method comprises the steps of piercing the wall of the cannula with a needle to form an aperture therein, withdrawing the needle from the aperture, driving the needle to rotate at high speed about its longitudinal axis, inserting the rotating needle in the aperture to contact the rim of the aperture as to cause frictional heating and consequently flow of material of the workpiece and thereby smooth out the rim contour.

SUMMARY

According to the invention there is provided a method for rounding at least a part of an edge of an opening in a tubular body formed of thermo-formable material, wherein a mandrel is brought into contact with the edge. The mandrel has a temperature that allows it to permanently deform the material of the tubular body. By bringing the mandrel into contact with the edge, it is possible to achieve a very precise and local deformation of the edge.

By providing a method where a heated mandrel is used to round at least a part of an edge of an opening in a tubular body, the rounding operation does not add any additional material to the tubular body or remove any material from the tubular body. This means that the operation does not contaminate the inside of the tubular body with excess or residual thereto-formable material.

Within the meaning of the present invention, the term thermo-formable material means any material which is suited for heating up to a predetermined temperature and thereafter stretched, molded, casted, pressed or formed into a predetermined shape in a way that the material retains its formed shape after cooling.

Furthermore, as the heated mandrel rounds at least parts of the edges of the opening in the tubular body, the internal edge of the opening is flushed with the internal surface of the tubular body, i.e. the edge would not project in a direction away from the internal surface of the tubular body towards the center of axis of the tubular body, and the fluid flow through the tubular body is not obstructed or constricted by the internal edges of the opening in the tubular body.

In general, the material of the tubular body may be any thermoplastic material, such as polyurethane, polyvinyl chloride, polyethylene and other thereto-formable materials. With respect of the present invention the meaning or understanding of the terms thermo-formable and thermoplastic is equivalent or synonymous.

It should be understood that the term 'rounding' applies to the process of evening out a sharp edge created by two abutting or adjacent surfaces or also further evening out an already relative smooth edge. Such a rounding may comprise a bevel or chamfer where the edge is removed in an angle, thus creating a third surface connecting the two previous abutting or adjacent surfaces. The rounding may also comprise a fillet, which creates a curved transition between the two surfaces.

In one embodiment of the present invention there is provided a method for rounding at least a part of an edge of an opening where the opening may not be circular. In some cases it is advantageous that the opening is not circular, as the size of the circumference of the tubular body would limit the maximal size of a circular opening. A circular opening having a diameter, which is close to the diameter of the tubular body would weaken the structural integrity of the tubular body considerably and the risk for unintentional bending of the tubular body would increase significantly.

In the case where a tubular body having a large opening may be required, it may be advantageous to increase the size of the opening, by providing an opening, which is larger in size in the longitudinal direction of the tubular body than the radial direction of the tubular body. In order to round at least a part of an edge of a non-circular opening, the mandrel would have to have the substantially same shape as the opening, such that the mandrel could be brought in contact with the edge of the opening.

Within the meaning of the present invention the term non-circular means having a form that is not in the form of a circle, i.e. that the form is not a closed plane curve where every point is equidistant from a fixed point within the curve. A non-circular form may be any suitable closed curve form, such as elliptical, oval or a n-sided polygon having n>2.

In order to improve deformation providing a quicker and more efficient process, the material may be heated to a temperature where it is moldable. This may for example be achieved by heating the mandrel to a temperature, which is equal to or larger than the glass transition temperature Tg of the material of the tubular body.

This allows the material to be heated above its glass transitional temperature, whereby the material is easier to deform.

In one embodiment the mandrel has a first proximal end having a first circumference smaller than the circumference of the opening and extends toward a second circumference area of the mandrel, which is larger than the circumference of the opening. This advantageously allows the edge to be rounded in one move, where the mandrel is moved axially into the opening pressed against the edge and out again.

By choosing different shaped mandrels different shaped rounded edges can be provided. Thus, the surface of the mandrel extending from the first cross sectional area to the second cross sectional area may extend in different shapes for example in a convex curve, concave curve, linear curve or in a combination thereof.

In other aspects of the invention a tubular body produced by the above method and a machine for producing such catheters is provided.

According to the invention, there is further provided a tubular body formed of thermo-formable material having at least one non-circular opening in the annular surface of the tubular body creating a fluid communication passage from the outside surface of the tubular body to the inside surface of the tubular body, the opening comprising an external edge abutting the outside surface and an internal edge abutting the inside surface, where the external edge of the opening is a substantially rounded edge.

The above-mentioned tubular body may advantageously be inserted into a body orifice or an incision or hole penetrating the skin of a user where the risk of injuring bodily tissue by the external edges of the tubular body is reduced, as the external edge of the non-circular opening is rounded and does not risk catching or becoming stuck in a bodily tissue, reducing the likelihood of the tearing or scratching of bodily tissue as a result thereof.

In one embodiment of the present invention the internal edge of the non-circular opening in the tubular body may be a substantially sharp edge. This means that the internal edge is substantially planar to the internal surface of the tubular body, such that fluid flow within the tubular body is not constricted by the inside edge of the non-circular opening.

In an other embodiment, the tubular body provides an unrestricted flow from the inside of the tip of the proximal end to the distal end. That is, no material is left in the tubular body as a result of forming the eyelets either as particulate matter, leftover matter, surplus matter or excess matter.

In yet another embodiment of the present invention the internal edge of the non-circular opening in the tubular body may become offset in a radial direction towards the central longitudinal axis of the tubular body. This may occur, in the case where the deformed material of the external edge is pressed or forced in a direction towards the internal edge, and the internal edge is displaced away from the deformed material. The displacement or offset of the internal edge does not affect the fluid flow or the actual throughput in the tubular body significantly.

Within the meaning of the present invention the term sharp edge means an edge that has not been rounded, and may be understood as an edge where two plane surfaces meet. The angle between the two plane surfaces may be in the range between approximately 70° and 120°. Furthermore, the area where the two plane surfaces meet may be blunt, in that the intersection between the two planes is not precise or well defined and the transition from one plane to the other may be gradual.

In one embodiment of the present invention the tubular body is a catheter. The rounded external edges of the non-circular openings reduce the risk that the external edges of the openings in the catheter would injure the mucosa during insertion of the catheter into the urinary channel.

The non-circular openings of the tubular body may be formed from a number of different shapes, where the shape of the opening may be selected from the group consisting of an ellipse, an oval or an n-shaped polygon having n>2. By having a non-circular opening, it is possible to increase the size of the opening, without reducing the structural strength of the tubular body significantly, as mentioned earlier. Based on the teaching of the present invention, it is obvious that different forms of non-circular openings could be used in the tubular body to provide fluid communication from the external surface of the tubular body towards the internal surface of the tubular body.

In one embodiment of the present invention, the substantially rounded external edge of the non-circular opening may be rounded by heating the external edge and deforming the external edge using heat-transferring means. This means that the non-circular opening may be of any form and the heat transferring means could be shaped in accordance with the form of the non-circular opening.

In one embodiment of the present invention, the heat transferring means may be a mandrel. The mandrel may be of the kind mentioned earlier having a form, which substantially conforms with the form of the non-circular opening. For example, if the non-circular opening is of an elliptical form the mandrel would also be of a substantially elliptical form.

FIGURES

Figure 2:
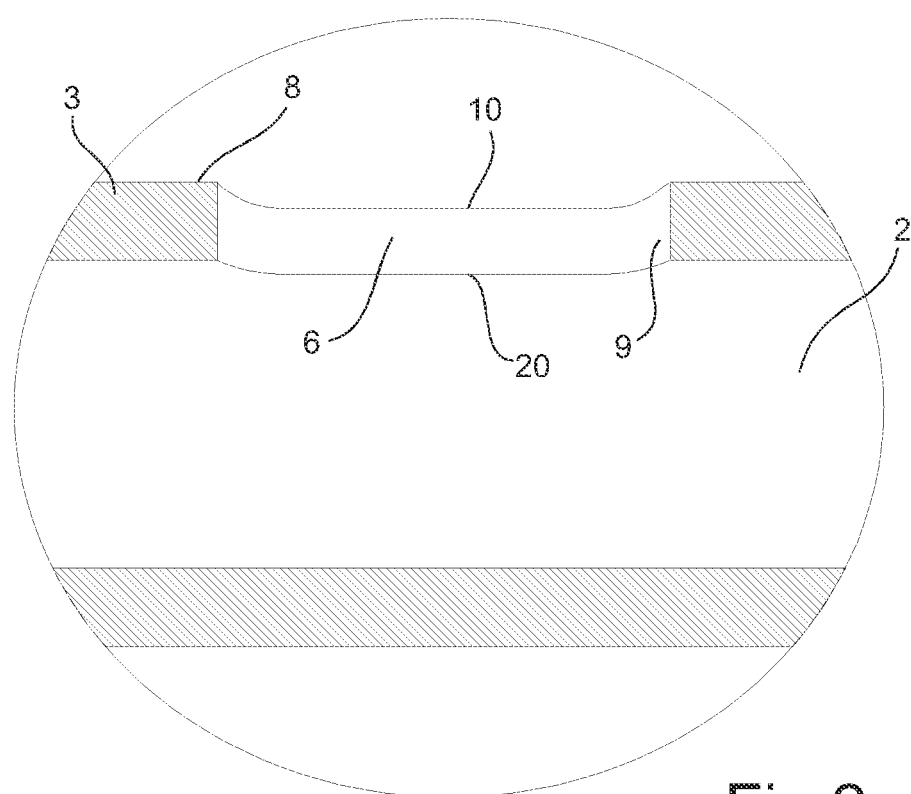
Figure 3:
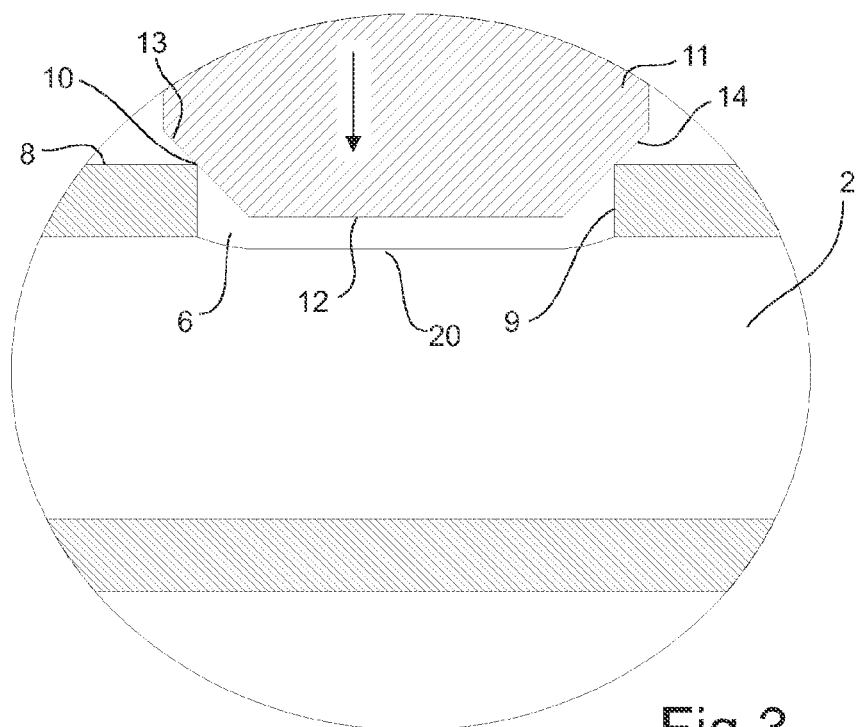
Figure 4:
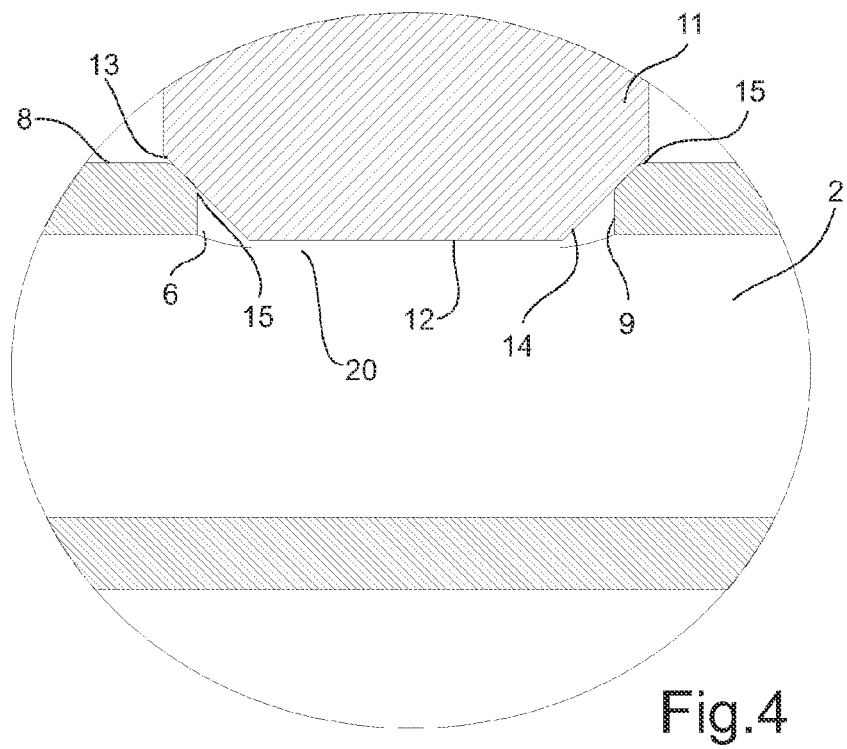
Figure 5:
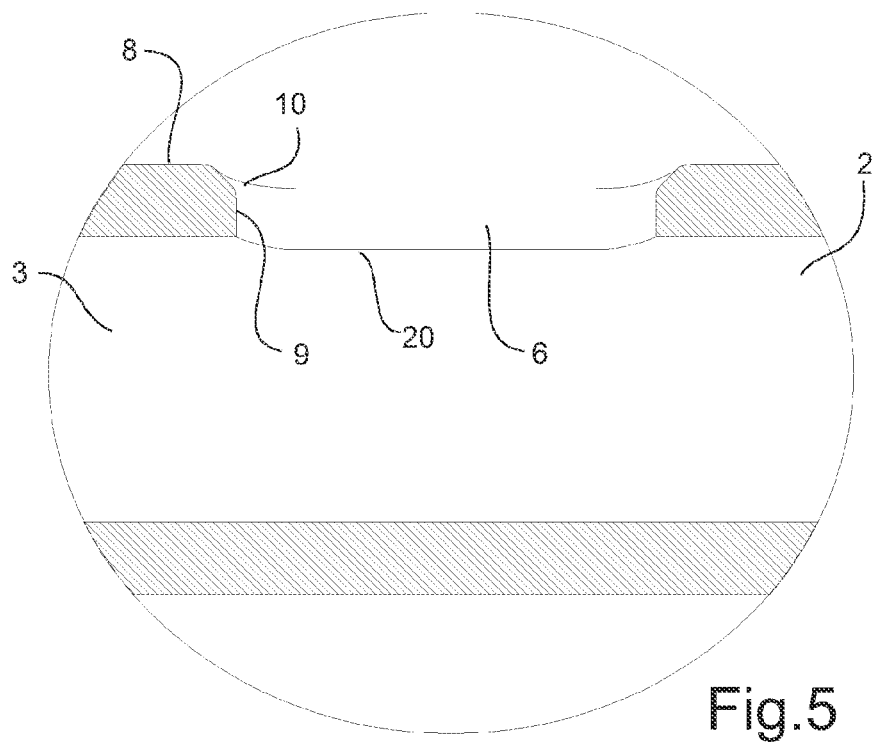
Figure 6:
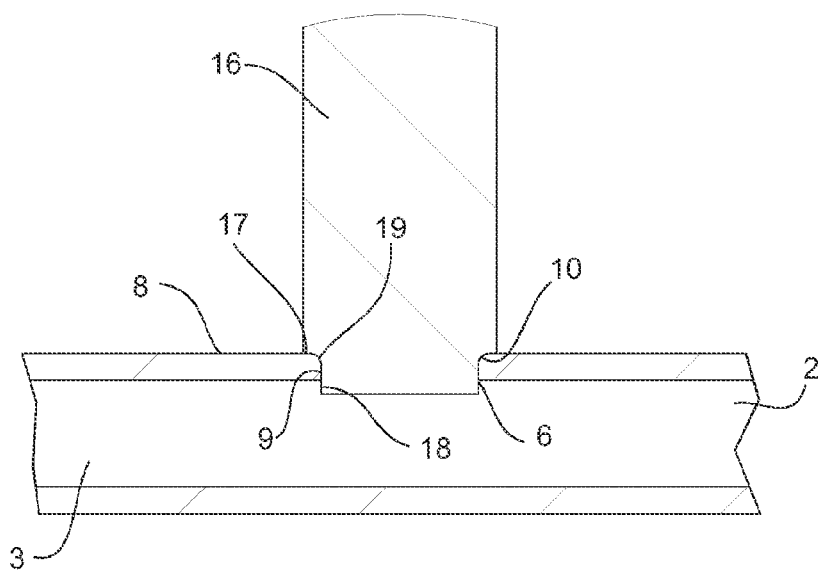

The invention will be explained in greater detail below, describing in example and referring to further advantages of the invention with reference to the drawing, in which FIG. 1 shows in cross section a traditional catheter, FIG. 2 shows in enlarged view and in cross section an untreated eyelet of the catheter above, FIG. 3 shows in enlarged view and in cross section the catheter above wherein a mandrel is brought into contact with the edge of the eyelet, FIG. 4 shows in enlarged view and in cross section the catheter above wherein a mandrel deforms the edge of the eyelet, FIG. 5 shows in enlarged view and in cross section the catheter above wherein the eyelet has been rounded, and FIG. 6 shows an alternative embodiment of a mandrel for use in the invention.

DETAILED DISCLOSURE

FIG. 1 shows a traditional intermittent catheter 1. The catheter is formed of a tubular body 2 having a rounded and closed off proximal end and a distal end 4, which is attached, e.g. by way of gluing to a connector 5.

At the proximal end there is formed a first and a second eyelet 6,7. This provides for fluid communication from the proximal end, through the catheter body and out through the connector.

Such eyelets can be provided in a number of different ways. One way is to simply punch out a hole. Alternatively, it can be drilled or otherwise cut.

FIG. 2 shows an enlarged view of the first eyelet 6. As can be seen the annular surface 8 of the catheter body and the inner surface 9 of the eyelet meets and creates an external edge 10 and an internal edge 20 where the inner surface 9 meets the inner surface 3 of the tubular body 2.

When inserting the catheter into the urethra there is a risk that the external edge injures the mucosa causing pain and irritation to the user. In worst case, it may lead to urinary tract infection.

In FIG. 3 a mandrel 11 is inserted into the eyelet. The mandrel has a proximal end 12, which has a circumference smaller than the circumference of the eyelet. The circumference of the mandrel increases from the proximal end 12 to a distal end 13 having a circumference, which is larger than the circumference of the eyelet. This allows a part of the mandrel to be inserted into the eyelet, in a way that the side 14 of the mandrel comes into contact with the external edge 10 of the eyelet.

By further pushing the mandrel into the eyelet, as can be seen in FIG. 4, the external edge 10 is deformed. This deformation is particularly facilitated when the mandrel is heated. Preferably the mandrel is heated to, or above, the glass transition temperature Tg of the material of the tubular body.

The mandrel can be made of many different heat conductive materials, such as for example copper, brass or steel. Additionally the mandrel can be coated, for example with Teflon allowing the material of the tubular body to easily release from the mandrel facilitating withdrawal of the mandrel from the eyelet. Alternatively, the mandrel is not coated but the surface of the mandrel is treated in other ways, for example by polishing, sanding, scratching or scraping the surface, in order to smoothen the surface or alternatively roughen it.

As may be noted, the radiating heat from the mandrel affects small areas 15 of the catheter that surrounds but is not in contact with the mandrel. This creates small rounded edges instead of sharp transition where the distal end 13 of the mandrel is not in contact with the tubular body. Adjusting the heat of the mandrel can advantageously control the curvature and deformation of these areas.

As the mandrel in the present embodiment only comes in contact with the external edge 10, the internal edge 20 is left intact and is planar to the inner surface of the tubular body.

As can be seen from FIG. 5 a rounded edge has thus been created, providing a smooth transition between the annular surface 8 and the inner surface 9. Thus, the risk of injuring the mucosa when the catheter is inserted into the urethra is decreased.

The method according to the invention allows for a high degree of control, as it is primarily the material in contact with the mandrel, which is deformed. Surrounding material is generally not affected and thus the risk of surrounding material melting and running into unwanted formations is considerably reduced.

An alternative embodiment of a mandrel 16 or use in a method according to the invention is shown in FIG. 6.

As can be seen the mandrel has a shoulder 17 and a neck 18. The surface of the shoulder is perpendicular to the surface of the neck. A rounded transition surface 19 connects the shoulder and neck in a curved fashion.

The circumference of the neck 18 is equal to (or slightly smaller than) that of the circumference of the inner surface 9 of the eyelet 6. This allows the neck to be inserted into the eyelet.

As the neck is moved into the eyelet the transition surface 19 comes into contact with the external edge 10. As the mandrel is heated to a temperature, which deforms the material of the tubular body when the mandrel gets into contact the external edge 10, the external edge will follow the curvature of the mandrel providing a smooth transition between the inner surface 9 and the annular surface 8 of the tubular body.

It is obvious based on the teachings of the present invention that the skilled person would adjust the technical parameters of the method, such as temperature of the mandrel, the mechanical pressure exerted by the mandrel on the external edges of the opening, the insertion speed of the mandrel or similar operational parameters based on choice of thermo formable material and the physical dimensions of the tubular body.

What is claimed is:

1. A method of treating a hole formed in a catheter, the method comprising:
   providing the catheter with an opening formed in a wall of the catheter from an external surface of the catheter to a longitudinal lumen of the catheter;
   heating a mandrel to provide a heated mandrel;
   inserting the heated mandrel into the opening formed in the wall of the catheter;
   rounding an external edge of the opening formed in the wall of the catheter with the heated mandrel; and
   leaving an internal edge of the opening unchanged and in a form of a sharp internal edge,
   wherein the sharp internal edge has an angle formed in a range from 70 degrees to 120 degrees as measured between the opening and an inside surface of the longitudinal lumen of the catheter.

2. The method of claim 1, comprising not pushing material of the wall of the catheter into the longitudinal lumen of the catheter.

3. The method of claim 1, wherein the sharp internal edge to has an angle formed at 90 degrees as measured between the opening and the inside surface of the longitudinal lumen of the catheter.

4. The method of claim 1, wherein the opening is a circular opening.

5. The method of claim 1, wherein the opening is elliptical and the heated mandrel inserted into the opening is elliptical.

6. A method of treating a hole formed in a catheter, the method comprising:
   providing the catheter with an opening formed in a wall of the catheter from an external surface of the catheter to an internal surface of a lumen of the catheter such that the catheter has a sharp external edge formed between the external surface and the opening and a sharp internal edge formed between the opening and the internal surface of the lumen of the catheter, with the sharp internal edge having an angle formed in a range from 70 degrees to 120 degrees as measured between the opening and the internal surface of the lumen of the catheter;

pushing a proximal end of a mandrel into the opening formed in the wall of the catheter and rounding the sharp external edge of the opening formed in the wall of the catheter with a distal end of the mandrel; and maintaining the sharp internal edge formed between the opening and the internal surface of the catheter.

7. The method of claim 6, comprising heating the mandrel to provide a heated mandrel and pushing the heated mandrel into the opening formed in the wall of the catheter.

8. The method of claim 7, comprising heating the mandrel to a temperature that is equal to or larger than a glass transition temperature of the material of the catheter.

9. The method of claim 6, wherein the proximal end of the mandrel has a circumference that is smaller than a circumference of the opening and the distal end of the mandrel has a circumference that is larger than the circumference of the opening.

10. The method of claim 6, wherein the mandrel has a shoulder, a neck that is perpendicular to the shoulder, and a rounded transition surface connected between the shoulder and the neck of the mandrel.

11. The method of claim 1, wherein providing the catheter comprises providing a urinary catheter.

\* \* \* \* \*